United States Patent
Richardson et al.

[11] Patent Number: 5,212,093
[45] Date of Patent: May 18, 1993

[54] METHOD TO DETERMINE DRIFT AND RESIDUAL OIL SATURATION

[75] Inventors: Edwin A. Richardson; Scott L. Wellington, both of Houston, Tex.

[73] Assignee: Shell Oil Company, Houston, Tex.

[21] Appl. No.: 738,645

[22] Filed: Jul. 31, 1991

[51] Int. Cl.$^5$ .................... G01N 33/24; E21B 47/10
[52] U.S. Cl. ........................ 436/27; 73/155; 166/250; 166/252; 436/30; 436/56; 436/161
[58] Field of Search ............ 166/250, 252; 73/155; 436/27, 30, 56, 161

[56] References Cited

U.S. PATENT DOCUMENTS

| | | | |
|---|---|---|---|
| 3,623,842 | 11/1971 | Deans | 436/27 |
| 3,751,226 | 8/1973 | Hesse et al. | 436/27 |
| 3,799,261 | 3/1974 | Deans et al. | 436/27 X |
| 3,847,548 | 11/1974 | Keller et al. | 436/27 |
| 3,856,468 | 12/1974 | Keller | 436/27 |
| 3,902,362 | 9/1975 | Tomich et al. | 166/250 X |
| 4,099,565 | 7/1978 | Sheely, Jr. et al. | 166/252 |
| 4,168,746 | 9/1979 | Sheely | 166/252 |
| 4,223,725 | 9/1980 | Teasdale et al. | 166/250 |
| 4,420,565 | 12/1983 | Schmitt | 436/27 |
| 4,722,394 | 2/1988 | Wellington et al. | 166/250 |
| 4,782,898 | 11/1988 | Wellington et al. | 166/252 |
| 4,782,899 | 11/1988 | Richardson | 166/252 |

OTHER PUBLICATIONS

Tomich et al., "Single-Well Tracer Method to Measure Residual Oil Saturation", *J. Petroleum Technology*, 1973, 25, 211–218.

C. Q. Sheely, "Description of Field Tests to Determine Residual Oil Saturation by Single-Well Tracer Method", *J. Petroleum Technology*, 1978, 30, 194–202.

*Primary Examiner*—James C. Housel
*Assistant Examiner*—Arlen Soderquist
*Attorney, Agent, or Firm*—Del S. Christensen

[57] ABSTRACT

Drift or residual oil saturation within a reservoir around a wellbore is determined by injection of a water-soluble tracer and then producing from the well. This injection is performed twice. The first injection is immediately followed by production in order to create a baseline. The second injection is followed by a soak period, and then production. Production of the tracers is compared to determine drift or residual oil saturation within the reservoir.

16 Claims, 1 Drawing Sheet

METHOD TO DETERMINE DRIFT AND RESIDUAL OIL SATURATION

FIELD OF THE INVENTION

This invention relates to methods to determine drift and residual oil saturation in a subterranean formation in the vicinity of a wellbore.

BACKGROUND TO THE INVENTION

A petroleum reservoir is typically a stratum of rock containing interconnected pore spaces which are saturated with oil, water, and/or gas. Knowledge of the relative amounts of these fluids in the formation, and residual oil saturation (ROS) in particular, is essential for planning of processes to recover oil from the reservoir and for estimating economic incentives to proceed with these processes.

Several methods have been utilized to determine ROS in oil reservoirs. Direct measurements may be obtained from a core sample. This can be very expensive. Additionally, there is also a high likelihood that the drilling required to obtain the sample will alter the fluid contents of the sample. Finally, coring only obtains information on fluid saturations at the point the core sample is obtained. Different regions of the reservoir have likely been exposed to recovery methods having a varying effectiveness.

Indications of ROS may also be obtained from well logs. This is relatively simple and inexpensive, but the data obtained are of limited accuracy. Data are only obtained for the formation that is within a few feet of the well. This portion of the formation has likely been disproportionately affected by production from the well. The logs also, by their nature, measure properties of the rock-fluid system. It is difficult to differentiate between the properties of the various fluid phases within the rock. The resultant estimates of ROS can therefore have significant errors.

ROS can also be approximated by performing material balances based on initial oil saturation and production histories. These estimates are subject to significant errors due to the dependence on knowledge of the amount of oil initially within the reservoir, and the difficulty of measuring and tracking accumulated oil and gas production.

In U.S. Pat. No. 3,623,842, a method to determine ROS is disclosed in which a hydrolyzable component in a carrier fluid is injected into the formation through a wellbore. This type of method is commonly referred to as a single well tracer test (SWTT). The component is one which partitions into both the oil and the water phases, and therefore propagates through the formation in a rate which is lower than the rate which the carrier fluids travel into the formation. The component is then permitted to remain in the formation for a "soak" period during which the component partially hydrolyzes, forming a product which is water soluble. After a portion, but not all, of the hydrolyzable component is hydrolyzed, fluids are produced from the well. The concentration of the hydrolyzable component and the water soluble hydrolysis product in the produced fluids are tracked. The product of the hydrolyzation will be produced with the produced fluid which was in the formation at the location of the hydrolyzable component during the soak period. The hydrolyzable component is not produced at that time because propagation back through the formation toward the well is delayed due to the partitioning between the oil and the water phases. The volume produced before the hydrolyzable component is produced, and the volume produced before the product of the hydrolysis is produced, along with the partitioning coefficients for each are then used to calculate the ratio of the two phases in the formation.

The method of '842 has been useful in many applications, but has shortcomings. The hydrolysis must consume a portion of the hydrolyzable component which results in measureable concentrations of both the hydrolyzable component and the product. The propagation of the hydrolyzable component into the formation is retarded due to partitioning between the mobile and the immobile phase. It would be preferred to have a component which is soluble only in the mobile phase injected into the formation because the ROS could then be determined at locations farther from the injection well. The hydrolyzable component must be one which does not significantly hydrolyze during the injection phase, but partially hydrolyzes during a soak period of a reasonable length under reservoir conditions. Hydrolysis of the potential hydrolyzable materials is very dependent upon conditions such as temperature and pH. These conditions can vary significantly from reservoir to reservoir. Suitable components are therefore dependent upon the particular reservoirs. Considerable planning and modeling must therefore go into ROS determination by this method.

A single-well tracer method which eliminates many of the problems of the method disclosed in '842 is disclosed in U.S. Pat. No. 3,856,468. This patent discloses injection of two water-soluble components in an aqueous carrier fluid into a well. One of the components is a precursor which reacts within the formation to form a partitionable tracer. The other component remains as a water-soluble tracer. After the components are injected and driven into the formation, they are allowed to soak. During this soak, the component which reacts to form the partitioning tracer does so. This method does not rely on a limited portion of the reactive component forming the tracer. Precursors can therefore be used in a wider variety of reservoir conditions. This method also eliminates the errors caused by the hydrolysis of the precursor occurring in the production phase. Additionally, the reservoir is tested farther from the well due to water soluble components being injected. This process therefore overcomes many of the shortcomings of the process disclosed in '842.

Although the components of patent '468 are said to be water soluble, they do have some oil solubility and may undergo some chromatographic separation in the process of being transported into the formation. Being different components, chromatographic separation differs for the different tracers. These things could cause the tracers to come back to the production well from different locations of the reservoir and would be undesirable.

Determination of ROS using the SWTT of patents '482 and '468 is also subject to considerable errors due to problems arising from interpretation of the data. The amount of tracers detected in the fluids produced from the well depends not only on the relative amount of oil, but also on drift, transient reactions, fluid loss and irreversible flow from the wellbore vicinity. When various combinations of these factors could be significant, a unique value for ROS cannot be determined due to the large number of variables which must be inferred in interpretation of the well test data. Tomich et al., in "Single-Well Tracer Method to Measure Residual Oil Saturation," *Journal of Petroleum Technology*, pp. 211-18, February 1973, discuss the effect of drift on the determination of ROS by SWTTs. A small scale mini-test is utilized to obtain better estimates of drift and reaction rate for use in designing a main test. The mini-test involves injection of a limited amount of ethyl acetate, allowing the ethyl acetate to partially hydrolyze in the formation, and then producing from the well. The limited amount of tracer injected prevents the mini-test from permitting determination of ROS with acceptable accuracy. Tomich claims that the mini-test is used to fine tune the test system and to estimate drift. But drift is estimated from the mini-test in the same way it is estimated from the main test. The mini-test, performed as Tomich performs the mini-test, only gives a second determination of drift. It does not yield an improved or more accurate measurement of drift.

Sheely, in "Description of Field Tests to Determine Residual Oil Saturation by Single-Well Tracer Method," *Journal of Petroleum Technology*, pp. 194-202, February 1978, discloses the incorporation of "irreversible flow" in accounting for the SWTT results. Drift and ROS could not account for the concentration profile of the tracer produced in a particular application. Sheely concludes that the SWTT can be useful, but is subject to considerable data interpretation. Applicants have further found that such data interpretation can result in multiple interpretations which each indicate a different ROS. It is preferable to have a method to determine ROS which does not rely on such data interpretation.

Determination of drift, fluid loss from the formation, irreversible flow from the formation have independent significance. Drift indicates the velocity at which fluids are moving in a formation. Such information is useful in planning locations of new wells and workovers of existing wells. Fluid loss from the formation and irreversible flow from the formation may indicate that fluids are communicating between layers in the formations. Such communications may be through wellbores which are improperly cemented. Knowing that this fluid loss is occurring could indicate that further remediation work is needed.

Prior art SWTTs which incorporate a hydrolyzable ester to generate tracers in-situ also suffer from hydrolyzation while the esters are in transit into the formation. Hydrolyzation rates are very pH dependent, being much faster at pHs above about 4 or 5. Because the generation of acid in-situ lowers the pH, rapid hydrolyzation can occur while the tracer precursors are being transmitted into the formation. This hydrolyzation is neglected by the prior art under the rationale that the time period is short compared to the soak. Neglecting these transient reactions introduces another source of error in interpretation of the single well tracer test data.

It is therefore an object of the present invention to provide a process to determine residual oil saturation or drift of a subterranean formation in the vicinity of a wellbore. In a preferred embodiment it is an object to provide such a process in which a water soluble tracer precursor is injected into the formation and within the formation transforms into a water-soluble tracer and a partitioning tracer.

SUMMARY OF THE INVENTION

According to the present invention a process to determine residual oil saturation in a formation is provided comprising the steps of:

performing a no-soak test consisting of (a) injecting into the formation through the wellbore, a mini-test aqueous solution comprising a tracer, which is at least partially water soluble, (b) producing from the wellbore without a soak period, and (c) determining the concentration of the tracers in the produced fluids as a function of the accumulated produced fluids;

performing a soak test consisting of (a) injecting into the formation through the wellbore a soak test aqueous solution comprising a precursor capable of forming, within the formation, a partitionable tracer which is partitionable between water and oil and a water soluble tracer which has greater water solubility and less oil solubility than the partitionable tracer, (b) neither injecting nor producing from the wellbore for a soak period, the soak period being of a duration at least long enough for a measurable amount of the partitionable tracer and the water-soluble tracer to form within the formation, (c) producing from the wellbore, and (d) determining the concentration of the partitionable tracer and of the water soluble tracer as a function of the accumulated produced fluids; and selecting a residual oil saturation which best accounts for the concentration of tracers as a function of the accumulated produced fluids from both the no-soak and the soak test.

A process to determine reservoir drift is also provided, the process comprising the steps of:

performing a no-soak test consisting of:
a) injecting into the formation through the wellbore an aqueous solution comprising a tracer which is at least partially water soluble,
b) producing from the wellbore without a soak period, and
c) determining the concentration of the tracer in the produced fluids as a function of the accumulated produced fluids, performing a soak test consisting of:
a) injecting into the formation through the wellbore a soak test aqueous solution comprising a tracer which is at least partially water soluble,
b) neither injecting nor producing from the wellbore for a soak period,
c) producing from the wellbore, and
d) determining the concentration of the tracer as a function of the accumulated soak test produced fluids;

determining dispersion from the concentration of the tracer in the no-soak test produced fluids as a function of accumulated produced fluids; and determining the drift of fluids within the formation by estimating the drift which would best account for the concentration of tracers in the soak test produced fluids as a function of accumulated produced fluids, at the dispersion determined from the no-soak test.

The no-soak test of the present invention may be utilized to estimate transient reactions of tracers, drift, fluid losses, and irreversible fluid flows from the formation in the vicinity of the borehole. These parameters are then utilized in interpretations of data from a single-well tracer test to determine residual oil saturation in the vicinity of the borehole. Knowledge of drift fluid losses and irreversible flow is independently useful, and may be determined by the no-soak test of the present process.

DETAILED DESCRIPTION OF THE INVENTION

Figure 1:
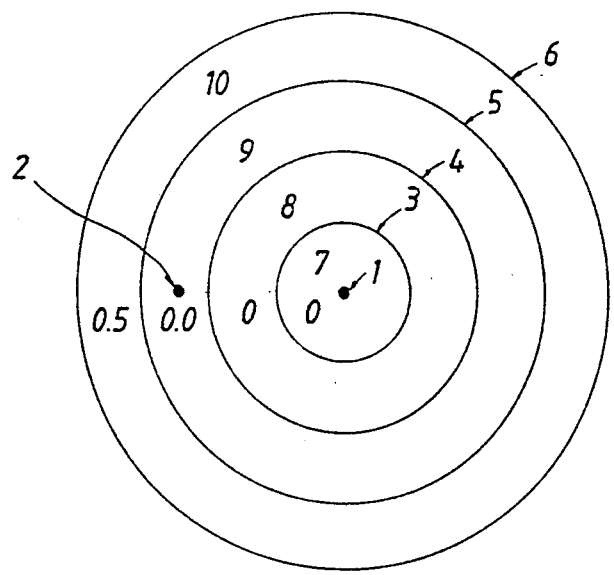
FIG. 1 shows the effect of drift on the location of a water-soluble tracer.

The present invention includes performance of a no-soak test in conjunction with a SWTT in order to determine either drift or residual oil saturation. SWTTs are described in U.S. Pat. Nos. 3,623,842 and 3,856,468 which may be modified according to the present invention. These patents are incorporated herein by reference. When residual oil saturation is to be determined, the soak test aqueous solution must contain a precursor such as those taught by these patents. A preferred precursor is one which is water soluble and forms both a water soluble and a partitionable tracer within the formation. Such precursors include dimethyl sulfonate, diamyl succinic acid, and amyl ethyl succinic acid sulfonate. These compounds generally hydrolyze to an alcohol, which is partitionable, and either an organic salt or acid or a short hydrocarbon chain alcohol which is water soluble. With a single precursor providing hydrolyzation products which are partitionable and which are water soluble, differential movement of precursors into the formation is avoided. Water soluble precursors are preferred to maximize the radius from the borehole which can be reached by the precursors.

Precursors which hydrolyze to yield both a partitionable and a water-soluble tracer are preferred over precursors which are partially hydrolized, and the remaining precursor functions as a tracer. Fully hydrolyzing the precursor eliminates the criticality of the length of the soak period. Transient reactions during the production cycle are also eliminated. Such a precursor is amyl ethyl succinic acid sulfonate. Amyl ethyl succinic acid sulfonate is water-soluble and hydrolyzes to form ethyl alcohol and amyl alcohol. Ethyl alcohol is water soluble and amyl alcohol partitions between water and oil. The half-life of amyl ethyl succinic acid sulfonate at 204° F. is about seven hours at a pH of 7.5, and about 30 hours at a pH of 6.5. At 175° F. and a pH of about 7, the half life is about 30 hours. These half lives are acceptable for many reservoirs.

When drift is to be determined, and not residual oil saturation, the purpose of the soak period is only to wait for movement of the tracers due to drift. Reactive tracers are not needed, and precursors which form partitionable tracers are not needed. Only a measurable amount of a water-soluble tracer need to be included in the injected solution.

In a preferred mode, drift and residual oil saturation are both determined based on one set of tests. Dispersion, or the spread of the tracers ahead and behind the main peak, is determined from the no-soak test. A soak test is performed to enable calculation of drift and residual oil saturation using the dispersion and transient reactions observed in the no-soak test.

The no-soak test can be accomplished by injecting an amount of an aqueous tracer containing solution. The amount is most preferably about equal to the amount in the soak test. Less solution is injected in the no-soak tests, then the dispersion must be corrected to take into account the difference in the distance traveled within the formation.

The no-soak test aqueous solution is preferably displaced into the formation by an inert drive such as brine. Brine, as it is used here, can be fresh water, salt water, seawater, or water from another formation. Any available water which is compatible with the formation could be utilized. The no-soak test aqueous solution is preferably pushed into the formation a distance of about 15 to about 25 feet from the wellbore.

SWTTs utilize principles of chromatography to calculate the ratio of oil to water in a formation. Knowing the pore volume and the percent of the pore volume filled with vapors (if any) from other known well logging techniques then allows calculation of the amount of oil remaining in the formation or residual oil saturation. Chromatographic separation occurs between a water-soluble tracer and a tracer which is partitionable between oil and water due to the water-soluble tracer moving through the formation at the speed that water moves through the formation while the partitionable tracer is adsorbed by immobile oil at the leading edge of a slug of the partitionable tracer, and then adsorbed again by water from the oil at the back end of the slug. The slug of partitionable tracer therefore moves through the formation at a reduced velocity which is dependent upon the relative amounts of oil and water within the formation.

Of course, only a significant difference in partitioning coefficients is required of the two tracers. Each of the so-called water-soluble tracers has some limited oil solubility, but the oil solubility of the water-soluble tracers is preferably low enough so that the water-soluble tracers travels through the formation at essentially the velocity at which water moves through the formation.

The ratio of oil to water is typically determined from a SWTT by the following general equation, after the produced volume of tracers from the soak test are corrected for drift:

$$\frac{S_o}{S_w} = \frac{V_P - V_{ws}}{\frac{V_{ws}}{K_p} - \frac{V_p}{K_{ws}}} \tag{1}$$

Where:
V is the volume of fluid produced from the formation between the start of the production cycle and the midpoint of a tracer slug;
K is the partition coefficient for the tracer between water and the oil expressed as the mass of the tracer per unit volume of water divided by the mass of the tracer per unit volume of oil at the reservoir temperature;
S is the saturation of a fluid expressed as a percent of total oil plus water volume of the formation.
Subscripts:
p = partitionable trace
ws = water-soluble trace
o = oil
w = water When $K_{ws}$ is much larger than $K_p$, this equation can be reduced to:

$$\frac{S_o}{S_w} = K_p(V_p/V_{ws} - 1) \tag{2}$$

$$\text{or } V_p = V_{ws}\left(\frac{S_o}{S_w K_p} + 1\right)$$

Without drift or irregularities of the formation in the vicinity of the wellbore, each tracer would arrive at the wellbore during the production phase as symetric peaks. The effect of drift is to cause the portion of the tracer which drifted toward the wellbore to be produced early, and the portion of the tracer which drifted away from the wellbore will be produced late. This causes the tracer in the produced fluids to be produced in a non-symetric fashion. Choosing the volumes to be used in equation 1 becomes difficult when the formation is subject to significant drift. This is because residual oil saturation, drift, and dispersion must all be inferred from one set of data. Considering problems which cause the data to be less than ideal, such as fluid loss, analytical limitations, background levels of components, and uniformity within the formation, inference of three variables from one set of data can easily lead to erroneous results.

The incorporation of the no-soak test according to the present invention provides an independent source of dispersion and drift, so only residual oil saturation is determined from the partitionable tracer concentration vs. accumulated produced fluid data set.

One algorithm to utilize the no-soak test data includes assuming that the no-soak test is a drift-free result, with only dispersion and formation properties accounting for the function of the return of the tracers in the produced liquids. The water-soluble tracer return in the soak test produced fluids different from the no-soak test produced fluid tracer contents only due to drift. The drift which best accounts for this difference is therefore the formation drift. With drift thus independently established, only the residual oil saturation must be varied to account for the differences between the concentration of water-soluble tracer and the partitionable tracer in the soak test produced fluids.

The effect of drift on the location of the water-soluble tracer is demonstrated in FIG. 1. The well borehole location at the time of injection is shown as 1. The wellbore hole location after drift has occurred is shown as 2. Concentric circles 3 through 6 separate regions of constant tracer concentrations 7 through 10 within the formation. These concentrations are marked on FIG. 1 as, for example, 0 for regions 7, 8, and 9, and as 0.5 for region 10. If there had been no drift, the produced fluids would be of tracer concentration of 0 until fluids from region 10 returned to the wellbore, at which time the tracer concentration would be about 0.5 until the fluids from region 10 are produced. With drift, fluids would be produced from production regions which do not coincide with regions which the fluids were initially injected into.

Figure 2:
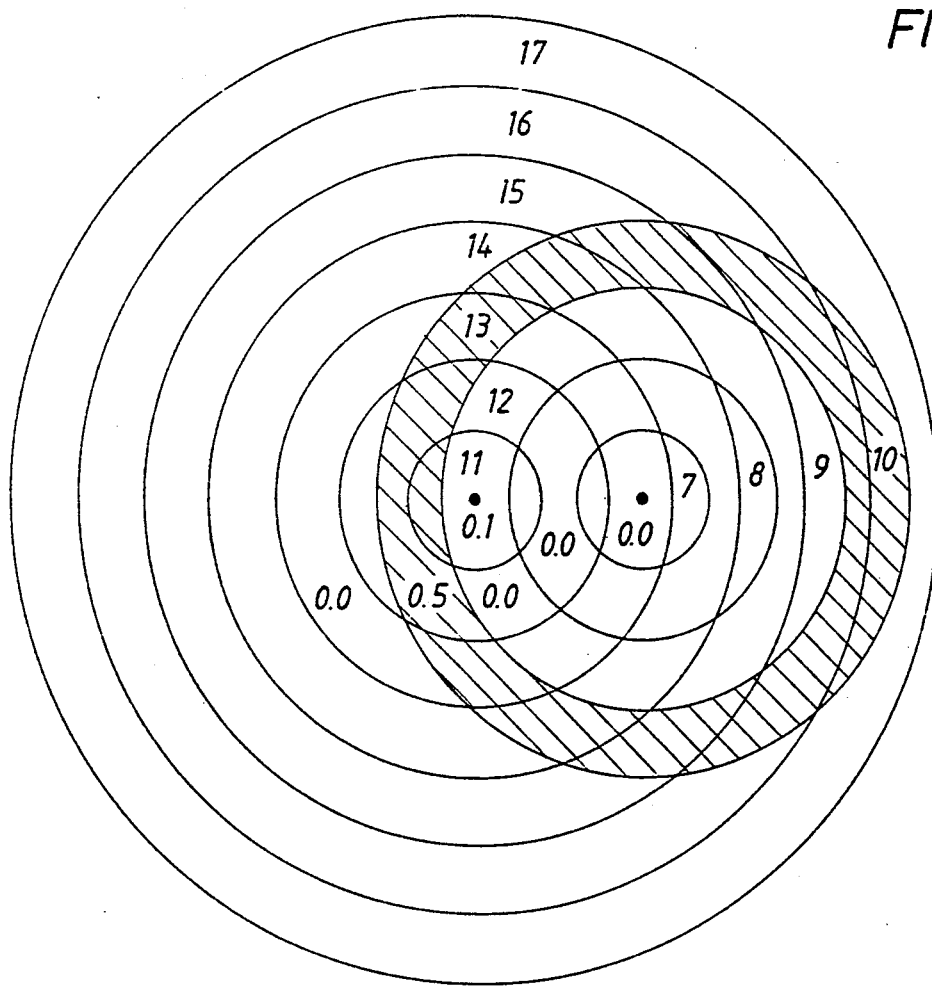
FIG. 2 is a graphical representation of a method to calculate drift and residual oil saturation according to the present invention.

FIG. 2 superimposes onto the FIG. 1 production regions 11 through 17. Produced fluids will be assumed to comprise of fluids within each consecutive region, starting with the region immediately surrounding the production wellbore, until essentially all of the tracer is produced. The concentration of tracer produced as fluids from each production region is the weighted average of the tracer concentrations within the volume of the production region. Computer modeling would permit the use of small incremental concentration regions and production regions, or the use of continuous functions to integrate curve-fit values. The no-soak test tracer return concentrations can be used to calculate tracer concentrations in regions around the wellbore at the start of the soak period. The above algorithm can then be used to estimate the expected concentration of water-soluble tracers in the soak test produced fluids as at different amounts of drift. The drift which most closely matches the observed return of the water-soluble tracer in the soak test is the estimate of drift. This match can be made visually or numerically by a weighted average least squares fit of the data to the different drift curves.

With the formation drift established, the residual oil saturation can then be determined from the soak test concentration of partitionable tracers in the produced fluids. The procedure for estimating the residual oil concentration is similar to that for estimating drift, except that curves for expected soak test partitionable tracer concentration is produced fluids as a function of accumulated produced fluids are generated, and the curve which best matches the observed concentration is selected as representing the formation residual oil saturation.

The methods disclosed by Tomich et al. in "Single-Well Tracer Method to Measure Residual Oil Saturation," *Journal of Petroleum Technology*, pp. 211–18 (February 1973), can be utilized to calculate the residual oil saturation which best fits the soak test results for partitionable tracer concentrations in the accumulated produced fluids.

We claim:

1. A process to determine residual oil saturation of a subterranean formation in the vicinity of a wellbore comprising the steps of:
    performing a no-soak test comprising (a) injecting into the formation through the wellbore a no-soak test aqueous solution comprising a tracer which is at least partially water soluble, (b) producing produced fluids from the wellbore without a soak period, and (c) determining the concentration of the tracer in the produced fluids as a function of the accumulated produced fluids;
    performing a soak test comprising (a) injecting into the formation through the wellbore, a soak test aqueous solution comprising a precursor capable of forming, within the formation, a partitionable tracer which is partitionable between water and oil and a water-soluble tracer which has greater water solubility and less oil solubility than the partitionable tracer, (b) neither injecting nor producing from the wellbore for a soak period, the soak period being of a duration at least long enough for a measurable amount of the partitionable tracer and the water-soluble tracer to form within the formation, (c) producing from the wellbore, and (d) determining the concentration of the partitionable tracer and of the water-soluble tracer as a function of the accumulated produced fluids; and
    selecting a residual oil saturation which best accounts for the concentration of tracers as a function of the accumulated produced fluids from both the no-soak test and the soak test.

2. The process of claim 1 wherein the tracer of the no-soak test is the same compound as the precursor of the soak test.

3. The process of claim 2 wherein the concentration of partitionable tracers are determined as a function of the accumulated produced fluids of the no-soak test; transient reactions are determined from the function of the concentration of partitionable tracers of the no-soak test, and the residual oil saturation is selected and corrected to account for the transient reactions.

4. The process of claim 1 wherein the precursor capable of forming a partitionable tracer is a water-soluble precursor which forms, under reservoir conditions, a water-soluble tracer and a partitionable tracer.

5. The process of claim 1 wherein the precursor is a hydrolyzable ester.

6. The process of claim 1 wherein injection of the soak test aqueous solution is followed by injection a first amount of brine to displace the soak test aqueous solution from the wellbore.

7. The process of claim 6 wherein injection of the no-soak test aqueous solution is followed by injection of a second amount of brine to displace the no-soak test aqueous solution from the wellbore.

8. The process of claim 7 wherein the amount of brine injected after the injection of the no-soak test aqueous solution is about equal to the amount of brine injected after the injection of the soak test aqueous solution.

9. A process to determine drift of reservoir fluids within a subterranean formation in the vicinity of a wellbore comprising the steps of:
performing a no-soak test comprising.
  a) injecting into the formation through the wellbore a first aqueous solution comprising a tracer which is at least partially water soluble,
  b) producing from the wellbore without a soak period, and
  c) determining the concentration of the tracer in the no-soak test produced fluids as a function of the accumulated produced fluids,
performing a soak test comprising.
  a) injecting into the formation through the wellbore a soak test aqueous solution comprising a tracer which is at least partially water soluble,
  b) neither injecting nor producing from the wellbore for a soak period,
  c) producing from the wellbore, and
  d) determining the concentration of the tracer as a function of the accumulated soak test produced fluids;
determining dispersion from the concentration of the tracer in the no-soak test produced fluids as a function of accumulated produced fluids; and
determining the drift of fluids within the formation by estimating the drift which would best account for the concentration of tracers in the soak test produced fluids as a function of accumulated produced fluids, at the dispersion determined from the no-soak test.

10. The process of claim 9 wherein the tracer of the no-soak test is the same compound as the tracer of the soak test.

11. The process of claim 9 wherein the tracer of the soak test is a precursor which forms, at reservoir conditions, a water-soluble tracer and a tracer which is partitionable between the oil and the water.

12. The process of claim 11 further comprising the step of determining the residual oil saturation by selecting a residual oil saturation which, at the dispersion determined from the no-soak test, best accounts for the soak test concentrations of water-soluble tracer and partitionable tracer in the soak test produced fluids as a function of accumulated produced fluids.

13. The process of claim 12 wherein the injection of the soak test aqueous solution is followed by injection a first amount of brine.

14. The process of claim 13 wherein the injection of the no-soak test aqueous solution is followed by injection a second amount of brine.

15. The process of claim 14 wherein the no-soak test aqueous solution is similar in amount and composition to the soak test aqueous solution.

16. The process of claim 15 wherein the first amount of brine injected is about equal to the second amount of brine.

* * * * *